(12) United States Patent
Lynch

(10) Patent No.: US 9,347,862 B2
(45) Date of Patent: May 24, 2016

(54) SETTING UP A WAFER INSPECTION PROCESS USING PROGRAMMED DEFECTS

(71) Applicant: KLA-Tencor Corporation, Milpitas, CA (US)

(72) Inventor: Graham Michael Lynch, Singapore (SG)

(73) Assignee: KLA-Tencor Corp., Milpitas, CA (US)

( * ) Notice: Subject to any disclaimer, the term of this patent is extended or adjusted under 35 U.S.C. 154(b) by 0 days.

(21) Appl. No.: 14/303,601

(22) Filed: Jun. 13, 2014

(65) Prior Publication Data

US 2015/0042978 A1    Feb. 12, 2015

Related U.S. Application Data

(60) Provisional application No. 61/862,777, filed on Aug. 6, 2013.

(51) Int. Cl.
| | | |
|---|---|---|
| G01N 21/00 | (2006.01) | |
| G01N 1/28 | (2006.01) | |
| G01N 21/95 | (2006.01) | |
| H01L 21/66 | (2006.01) | |

(52) U.S. Cl.
CPC .............. *G01N 1/28* (2013.01); *G01N 21/9501* (2013.01); *H01L 22/12* (2013.01); *H01L 22/30* (2013.01)

(58) Field of Classification Search
CPC .................. H01L 2924/00; H01L 2924/0002; H01L 27/0207; H01L 27/0886; H01L 21/823431; H01L 23/585; H01L 27/1116; H01L 27/1225; H01L 27/3223; H01L 2924/01322; H01L 2924/1306; H01L 2924/13091
See application file for complete search history.

(56) References Cited

U.S. PATENT DOCUMENTS

| | | |
|---|---|---|
| 6,038,019 A | 3/2000 | Chang et al. |
| 6,583,870 B2 | 6/2003 | Noda |
| 6,617,084 B2 | 9/2003 | Ki |

(Continued)

FOREIGN PATENT DOCUMENTS

| | | |
|---|---|---|
| EP | 1 430 514 | 6/2004 |
| JP | 06-216207 | 8/1994 |

(Continued)

OTHER PUBLICATIONS

International Search Report and Written Opinion for PCT/US2014/050017 mailed Nov. 18, 2014.

(Continued)

*Primary Examiner* — Michael P Stafira
(74) *Attorney, Agent, or Firm* — Ann Marie Mewherter

(57) ABSTRACT

Methods and systems for setting up a wafer inspection process using programmed defects are provided. One method includes altering a design for a dummy area of a production chip such that printing of the dummy area on a wafer results in printing of a variety of defects. Two or more of the defects have different types, one or more different characteristics, different contexts in the design, or a combination thereof. The dummy area printed on a wafer may then be scanned with two or more optical modes of an inspection system to determine which of the optical mode(s) are better for defect detection. Additional areas of the wafer may then be scanned with the optical mode(s) that are better for defect detection to determine noise information. The noise information may then be used to select one or more of the optical modes for use in a wafer inspection process.

37 Claims, 4 Drawing Sheets

(56) References Cited

U.S. PATENT DOCUMENTS

| | | |
|---|---|---|
| 6,635,872 B2 | 10/2003 | Davidson |
| 7,397,556 B2 | 7/2008 | Patterson et al. |
| 7,446,868 B1 | 11/2008 | Higgs et al. |
| 7,656,170 B2 | 2/2010 | Pinto et al. |
| 8,250,496 B2 | 8/2012 | Moon |
| 8,289,508 B2 | 10/2012 | Lim et al. |
| 8,487,644 B2 | 7/2013 | Huang et al. |
| 2003/0201410 A1 | 10/2003 | Nagamura |
| 2008/0084223 A1 | 4/2008 | Lee et al. |
| 2008/0163140 A1* | 7/2008 | Fouquet et al. .......... 716/4 |
| 2011/0276935 A1* | 11/2011 | Fouquet et al. .......... 716/112 |
| 2011/0296362 A1* | 12/2011 | Ishikawa et al. .......... 716/112 |
| 2011/0320149 A1 | 12/2011 | Lee et al. |
| 2012/0308112 A1* | 12/2012 | Hu et al. .......... 382/149 |

FOREIGN PATENT DOCUMENTS

| | | |
|---|---|---|
| WO | WO 01/06043 | 1/2001 |
| WO | WO 2008/070772 | 6/2008 |

OTHER PUBLICATIONS

Bonam et al., "E-beam Inspection of EUV Programmed Defect Wafers for Printability Analysis," ASMC 2013, 310-314, May 16, 2013.

* cited by examiner

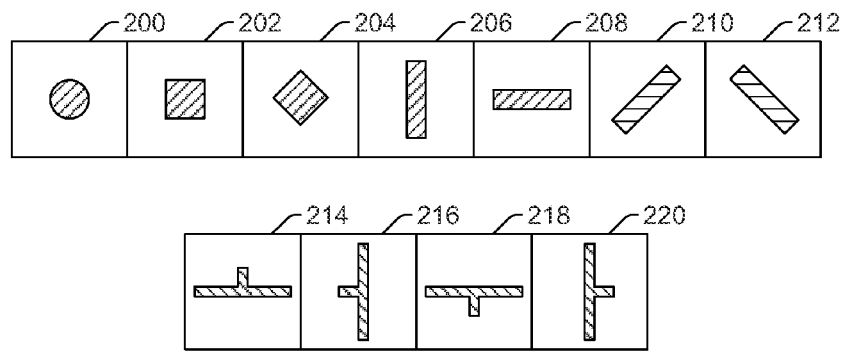
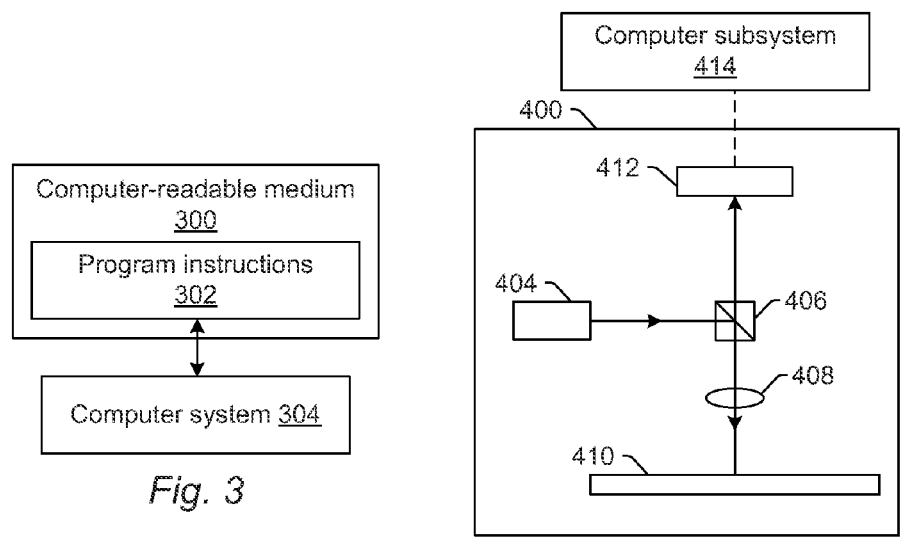
Fig. 2
Fig. 3
Fig. 4

SETTING UP A WAFER INSPECTION PROCESS USING PROGRAMMED DEFECTS

BACKGROUND OF THE INVENTION

1. Field of the Invention

This invention generally relates to setting up a wafer inspection process using programmed defects.

2. Description of the Related Art

The following description and examples are not admitted to be prior art by virtue of their inclusion in this section.

Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing (CMP), etch, deposition, and ion implantation. Multiple semiconductor devices may be fabricated in an arrangement on a single semiconductor wafer and then separated into individual semiconductor devices.

Inspection processes are used at various steps during a semiconductor manufacturing process to detect defects on wafers to promote higher yield in the manufacturing process and thus higher profits. Inspection has always been an important part of fabricating semiconductor devices such as ICs. However, as the dimensions of semiconductor devices decrease, inspection becomes even more important to the successful manufacture of acceptable semiconductor devices because smaller defects can cause the devices to fail.

There are a number of currently used methods for setting up inspection process recipes. For example, one current method includes taking a wafer (covered in chips) with an unknown number and location of patterned defects (potentially none) and inspecting the wafer with "historically commonly used modes" and a substantially low threshold. The substantially low threshold means that a substantial amount of noise will likely be detected together with defects of interest and all of the detected events need to be reviewed arduously on a scanning electron microscope (SEM) until at least a few pattern defects are found and separated from the noise. Then, the pattern defect locations can be driven to on the inspector to check all or most of the modes to see which has the highest signal for the defects already found.

One disadvantage of this method is that choosing the optimum mode is often unintuitive. For example, the shortest available wavelength on a wafer inspection system doesn't always provide the best signal for a given defect type. In addition, most of the production wafers used for bright field (BF) recipe setup will not contain all types of pattern defects ("types" being a combination of size, shape, location, etc.) or even a very limited number of any one type of pattern defect of interest. As such, the best mode for each potential defect type cannot be known without using many, many wafers for mode data collection. Therefore, data collection takes a significant time or, more often, a fab chooses to take a chance on a limited signal/noise data set thereby running the risk of missing certain killer defect types, which would cause wafer yield crashes and lead to less sellable chips.

Another currently used method involves placing programmed defects inside test chips (as opposed to product/sellable chips), and the best mode is found using those programmed defects. Noise information is also gathered on the test chips. However, test chips cannot represent all types of production chips. In addition, the production chips can vary widely in background pattern. The background pattern under and next to a programmed defect will alter the mode that is best at catching it. Therefore, if there are differences in the background pattern of the test chip and the product or sellable chip, then it is possible that the mode selected as the best mode using the test chip may not actually be the best mode for detecting the defects in the product chip. Furthermore, often, test chips are run on a process that evolves over time. Therefore, if a best mode was selected using programmed defects on a test chip, it may no longer apply to current production chips.

An additional currently used method involves placing programmed defects in scribe areas on a wafer. The scribe areas may be next to test chips or product/sellable chips. The best mode may then be found using these programmed defects. Such methods also, however, have a number of disadvantages. For example, the noise data may not be collected at all or may be only collected on the scribe structure. Therefore, the noise data may be local noise and not representative of the true wafer-wide or chip-wide worst case scenario for noise. In addition, the background pattern and typically the film stacks and film uniformity are different in the scribe lane compared to that in-die on production chips. For example, the scribe lanes typically contain test pads and targets for measuring thickness, overlay, critical dimensions, etc. These differences can lead to selection of a mode that is the best for detection of defects in the scribe lane but that is not the best for detecting defects in the production chip, which is where inspection really matters. Furthermore, the scribe area will later be used to cut up the wafer (for dicing) thereby separating the chips, so control of the process in these areas is typically far poorer that in-die controls because the scribe area has no direct impact on chip functionality and yields. Therefore, picking the best mode(s) using programmed defects placed in the scribe area is likely to lead to the wrong mode being selected since there are significant differences between scribe and in-die areas.

Accordingly, it would be advantageous to develop methods and/or systems for wafer inspection setup that do not have one or more of the disadvantages described above.

SUMMARY OF THE INVENTION

The following description of various embodiments is not to be construed in any way as limiting the subject matter of the appended claims.

One embodiment relates to a method for setting up a wafer inspection process. The method includes altering a design for a dummy area of a production chip such that printing of the dummy area on a wafer results in printing of a variety of defects. Two or more of the defects have different types, one or more different characteristics, different contexts in the design, or a combination thereof. The method also includes scanning the dummy area of a wafer on which the altered design is printed with two or more optical modes of an inspection system thereby generating output with one or more detectors of the inspection system for each of the two or more optical modes. In addition, the method includes selecting at least one of the two or more optical modes of the inspection system that resulted in the output that is better for detection of one or more of the defects than the output produced by others of the two or more optical modes. The method further includes scanning additional areas on the wafer with the at least one selected optical mode of the inspection system thereby generating additional output with the inspection system. The method also includes selecting one or more of the at least one selected optical mode that resulted in the output and the additional output that are best for the detection of the one or more of the defects for use in the wafer inspection process. The altering and selecting steps are performed with one or more computer systems.

The method described above may be performed as described further herein. In addition, the method described above may include any other step(s) of any other method(s) described herein. Furthermore, the method described above may be performed by any of the systems described herein.

Another embodiment relates to a non-transitory computer-readable medium storing program instructions executable on a computer system for performing a computer-implemented method for setting up an inspection process. The computer-implemented method includes the steps of the method described above. The computer-readable medium may be further configured as described herein. The steps of the computer-implemented method may be performed as described further herein. In addition, the computer-implemented method for which the program instructions are executable may include any other step(s) of any other method(s) described herein.

An additional embodiment relates to a wafer inspection system that includes one or more computer subsystems configured for altering a design for a dummy area of a production chip such that printing of the dummy area on a wafer results in printing of a variety of defects. Two or more of the defects have different types, one or more different characteristics, different contexts in the design, or a combination thereof. The wafer inspection system also includes an optical subsystem configured to scan the dummy area of a wafer on which the altered design is printed with two or more optical modes of the optical subsystem thereby generating output with one or more detectors of the optical subsystem for each of the two or more optical modes. The one or more computer subsystems are further configured for selecting at least one of the two or more optical modes of the optical subsystem that resulted in the output that is better for detection of one or more of the defects than the output produced by others of the two or more optical modes. The optical subsystem is also configured to scan additional areas on the wafer with the at least one selected optical mode of the optical subsystem thereby generating additional output with the optical subsystem. The one or more computer subsystems are also configured for selecting one or more of the at least one selected optical mode that results in the output and the additional output that are best for detection of the one or more of the defects for use in the wafer inspection process. The wafer inspection system may be further configured as described herein.

BRIEF DESCRIPTION OF THE DRAWINGS

Other objects and advantages of the invention will become apparent upon reading the following detailed description and upon reference to the accompanying drawings in which:

FIG. 2 is a schematic diagram illustrating plan views of various embodiments of defects that may be included in a design altered as described herein and various embodiments of contexts in the design for the defects;

FIG. 3 is a block diagram illustrating one embodiment of a non-transitory computer-readable medium storing program instructions executable on a computer system for performing one or more of the computer-implemented methods described herein;

FIG. 4 is a schematic diagram illustrating a side view of one embodiment of a wafer inspection system.

Figure 1:
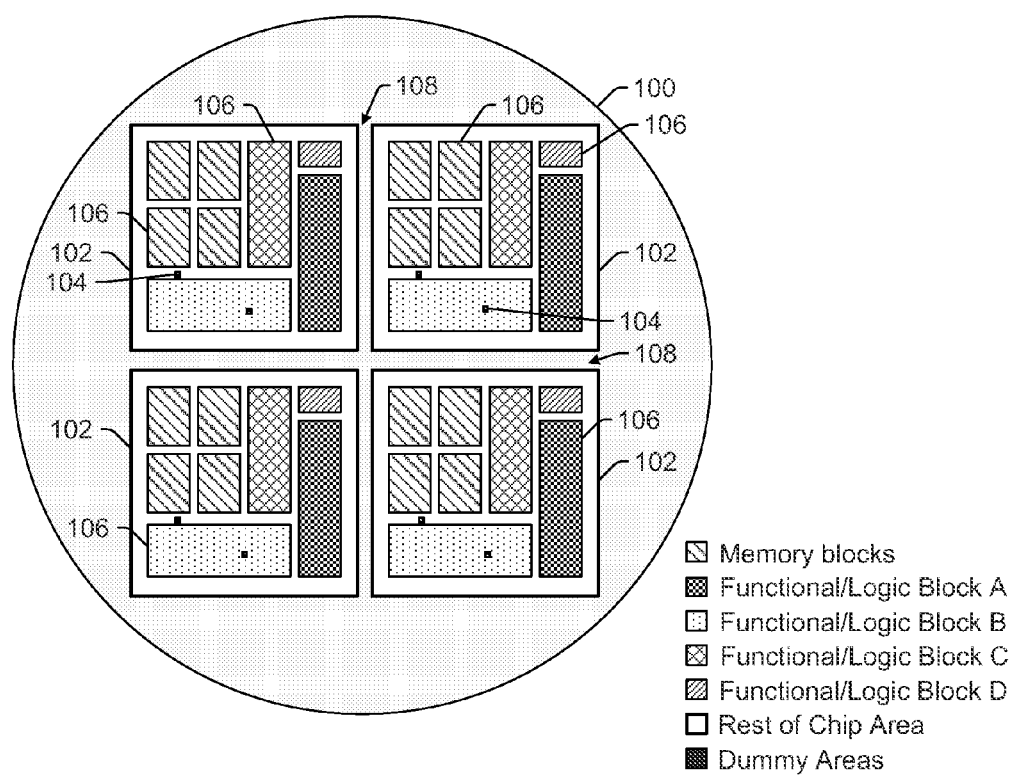
FIG. 1 is a schematic diagram illustrating a plan view of one embodiment of a wafer that includes multiple production chips formed thereon, each of which includes dummy areas.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals. Unless otherwise noted herein, any of the elements described and shown may include any suitable commercially available elements.

The embodiments described herein generally relate to methods and systems for selecting the best "inspection mode(s)" for production chips (including fabless chips) using programmed defects embedded in the dummy pattern area of those chips. For example, one embodiment relates to a method for setting up a wafer inspection process. The method includes altering a design for a dummy area of a production chip such that printing of the dummy area on a wafer results in printing of a variety of defects, as shown in step 500 of FIG. 5. Therefore, the method includes altering a design for a dummy area of a production chip to include programmed defects. In one embodiment, the defects are pattern defects, and altering the design includes adding patterned features, removing patterned features or adding and removing patterned features in the design for the dummy area. For example, programmed defects are defects that are typically defined as pattern defects (versus particles and other foreign material) that are seen at the wafer level, but are deliberately created by adding and/or removing patterns at the pattern design/layout and then mask making stages (i.e., before the wafer is printed with the mask).

The production chip is not a test chip. In addition, the dummy area is not a scribe line area on the wafer. For example, the embodiments described herein place "programmed defects" inside a functioning chip in what has been known as "dummy pattern" areas in chips that would typically be sold to make consumer electronic and other products (as opposed to 1) programmed defects being placed in "test chips" which are used primarily to debug a new chip making process and are often not sold or 2) programmed defects being placed in the "scribe" area which is directly next to, but still outside of, the chips themselves). Therefore, the embodiments described herein replace the dummy pattern without programmed defects in production chips with the dummy pattern with programmed defects inside production chips, instead of using test chip or scribe lane structures for placement of programmed defects.

FIG. 1 illustrates one embodiment of a wafer layout that is included herein to illustrate the various areas described herein. For example, FIG. 1 shows wafer 100 having a plurality of dies 102 formed thereon. In the embodiment shown in FIG. 1, dies 102 are production chip dies in that the dies are being used to form production chips that will be sold commercially or included in commercially sold products. Although only four dies 102 are shown formed on the wafer in FIG. 1, the wafer may have any suitable arrangement and number of dies formed thereon.

Each of the dies formed on the wafer may include device area(s) and dummy area(s). For example, in the embodiment shown in FIG. 1, dies 102 include dummy areas 104 and device areas 106. In addition, as shown in FIG. 1, the device areas include different types of device areas. In particular, as shown in the legend for FIG. 1, the device areas can include memory blocks (containing repeating patterns) and different types of functional or logic blocks (e.g., functional/logic block A, functional/logic block B, functional/logic block C, and functional/logic block D). In addition, the dies may include dummy areas located in different places within the dies. For example, as shown in FIG. 1, one of the dummy areas 104 can be located in the non-device area of the chip (e.g., as shown by the "rest of chip area" in the legend of FIG. 1), which is between different device areas and still within the production chip. The "rest of chip area" is generally used to connect functional blocks within the chip and a large percentage of this area is often filled with dummy patterns. In addition, another dummy area 104 can be located in one of the device areas of the chip (e.g., in functional/logic block B as shown in FIG. 1). The production chips described herein can include any arrangement of such dummy areas (e.g., one or more dummy areas in a non-functional area of the chip and/or one or more dummy areas within a functional device area of a chip).

Although the dummy areas can be located within the device areas in the production chip, in general, the dummy and device areas do not overlap within the dies or on the wafer. For example, dummy features located in dummy areas of the chip (regardless of where the dummy areas are located) will not also be device features. The dummy area will generally include dummy pattern features that is, pattern features that will not become or form any functioning part of the final production chip. Instead, dummy pattern features may be formed in various areas of a die or chip to alter how other features are formed in the die or chip or to be used for testing purposes. In contrast, features that are formed in the device areas of the chip will become functioning parts of the final production chip.

The configuration (e.g., size, shape, location, etc.) of the dummy and device areas shown in FIG. 1 is merely one example that is used to illustrate the various features of the embodiments described herein and is not meant to be representative of any actual production chip or to limit the embodiments described herein. For example, the dummy and device areas may have different shapes and dimensions than those shown in FIG. 1, and the configuration would still be within the scope of the embodiments described herein. In addition, the production chips may include more than one dummy area in any one of the production chips, and the programmed defects described herein may be included in any one or more of those dummy areas.

Figure 1A:
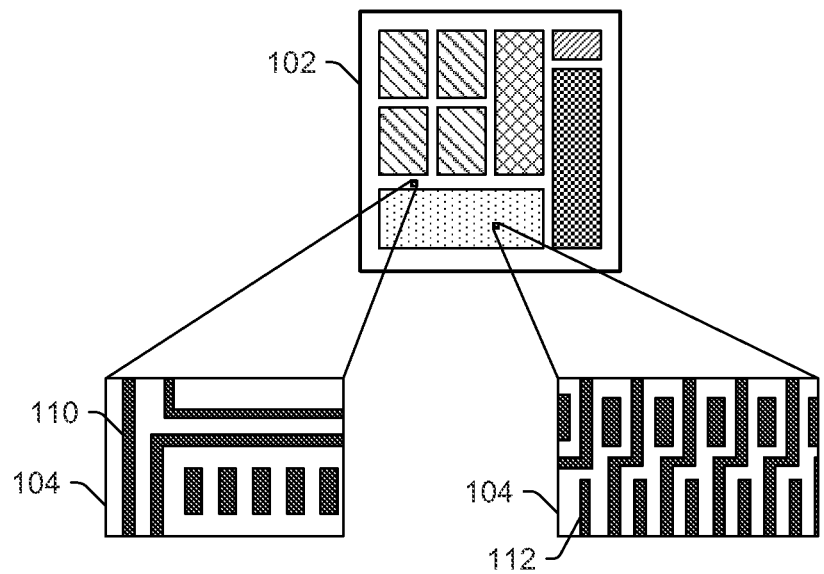
FIG. 1a is a schematic diagram illustrating a plan view of one embodiment of a production chip of FIG. 1 with two of its dummy areas (without programmed defects) shown in exploded views.
Figure 1B:
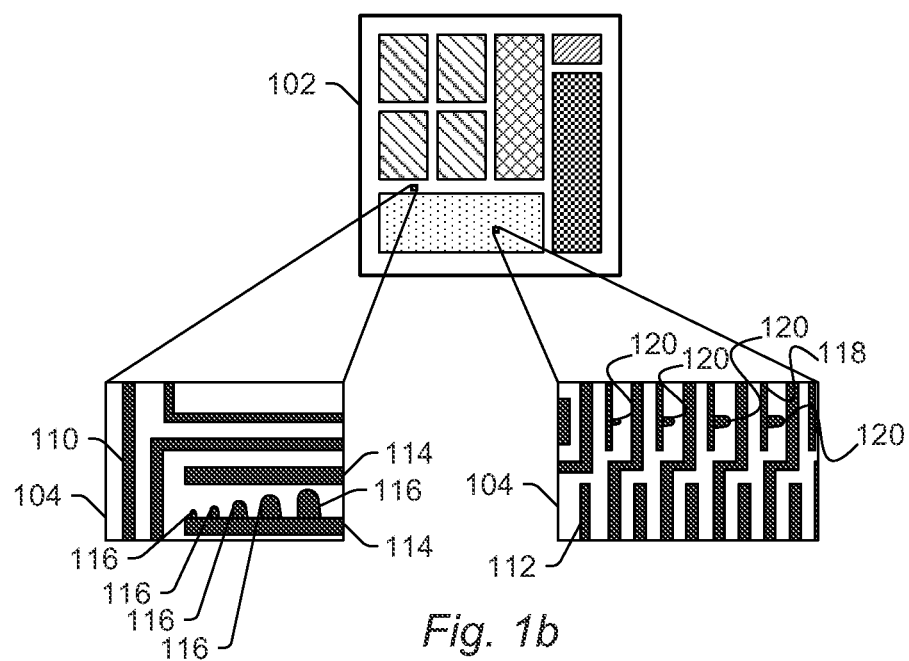
FIG. 1b is a schematic diagram illustrating a plan view of one embodiment of a production chip of FIG. 1 with two of its dummy areas (with programmed defects) shown in exploded views.

FIGS. 1a and 1b illustrate one example of how the dummy pattern without programmed defects in production chips can be replaced with the dummy pattern with programmed defects inside production chips. For example, as shown in FIG. 1a, one of the dummy areas 104 may include one set of dummy features 110, and another of the dummy areas 104 may include another set of dummy features 112. These dummy features illustrate different examples of a dummy pattern without programmed defects. In contrast, as shown in FIG. 1b, some of the dummy features included in the dummy areas may be replaced with or altered by programmed defects. For example, as shown in FIG. 1b, some of dummy features 110 shown in FIG. 1a have been replaced by new dummy features 114 with programmed defects 116 added. In addition, as shown in FIG. 1b, some of dummy features 112 shown in FIG. 1a have been replaced by new dummy features 118 with programmed defects 120 added. Therefore, as can be seen in FIG. 1b, the dummy pattern with programmed defects can be added to dummy areas located in functional areas of the chip and in between the functional pattern areas of the chip.

It is to be noted that the patterns shown in FIGS. 1a and 1b are the "as-designed" patterns. In other words, the patterns shown in FIGS. 1a and 1b do not represent features that did not print correctly on a wafer and are therefore defects or defective. Instead, the patterns shown in FIGS. 1a and 1b illustrate how the features are represented in the design data for the wafer. How these patterns print on wafers and therefore appear on the wafers may be different than what is shown in these figures.

Using the dummy pattern area for programmed defect placement is possible because most production chips have a significant percentage of their area used for dummy patterns on all or most layers (for example, greater than 0.1% of the chip area). The programmed defects described herein can fit into an area that is less than 0.1% of the chip area and still be useful for optimum mode selection.

As further shown in FIG. 1, scribe lanes 108 include areas between each of the production chip dies 102 on the wafer. Therefore, the scribe lanes are outside of the dies and adjacent to the dies. As such, the scribe lane areas and the die areas do not overlap on the wafer.

Two or more of the defects have different types, one or more different characteristics, different contexts in the design, or a combination thereof. For example, two or more of the defects may have different defect shape characteristics. In one such embodiment, as shown in FIG. 2, the defects that are included in or programmed into a design for one dummy area may include defects 200, 202, 204, 206, 208, 210, and 212 that each have different shapes from each other. Of course, the shapes shown in FIG. 2 are merely meant to be representative of a few of the possible defect shape types that may be programmed into the dummy area design. The actual shapes of the programmed defects will vary depending on the types of defects that are of interest to users. In addition, the defects may include two or more defects that have one characteristic that is the same and vary in another characteristic. For example, the design for the dummy area may be altered to include more than two defects having the same shape as defect 200 shown in FIG. 2, and each of the defects may have different sizes.

The defects may also include two or more defects that have the same shape and/or different contexts in the design. In one such example, the design for the dummy area may be altered to include more than two defects having the same shape as defect 200 shown in FIG. 2, each of which is located in a different context in the design. In one such embodiment, the design for the dummy area may be altered to include at least one defect such as defect 200 in each of different contexts 214, 216, 218, and 220 shown in FIG. 2 that may represent the device structures in the production chip. Of course, the contexts shown in FIG. 2 are merely meant to be representative of a few of the possible defect context types that may be programmed into the dummy area design. The actual contexts of the programmed defects will vary depending on the types of defect contexts that are of interest to users. Therefore, the dummy area design may be altered to include the same defect sitting on different background patterns.

More than one of such defects may be located in the same context with the same shape, but different sizes. Various such embodiments are shown in FIG. 1*b*. In particular, as shown FIG. 1*b*, programmed defects 116 are each located in roughly the same context and have the same shape, but have different heights and different widths. In addition, programmed defects 120 are located in the same context and have the same shape as each other, but each of these programmed defects have different heights and different widths than each other programmed defect.

Therefore, the deliberately created, so called "programmed (pattern) defects" if placed inside the chip can be effectively used to represent all types of pattern defects that may occur anywhere inside that chip. In theory, any defect shape/size could occur randomly in a device. So, to test the ability of an inspection system to capture every possible defect, then ideally as many different shapes and sizes of defects would be "programmed" in the dummy area as space on the production chip will allow. In some instances, the space in the dummy area for programmed defects may be limited. In these cases, the defects having different characteristics (e.g., the shapes and sizes) that are programmed into the dummy area design may be prioritized. Prioritization may vary depending on the application, but one method of prioritization may be based on the ability of the defects to kill the device being formed with the production chip. For example, bridge or near-bridge defects that are between lines of patterns may be given a higher priority than defects in wide open spaces with no pattern nearby. In addition, the defect sizes may be selected to be of a similar size to the pattern being printed (not so much bigger than the pattern that the inspection system is certain to catch the defect in every possible mode (or every mode tested) and not so much smaller versus the pattern that the defect could never cause a bridge or an open).

The design for the dummy area can also be altered to include the programmed defects while ensuring that the in-die dummy pattern used as the background pattern (or context) for the in-die programmed defects well represents the patterns, structures, line widths, etc, of the production chips. As such, in one embodiment, the different contexts in the design include different patterned features that have the same characteristics (e.g., shape, size, orientation, etc.) as corresponding patterned features in a device area of the production chip. In addition, since the programmed defects are not placed in test dies or in the scribe lane area of the wafer, the characteristics of the wafer layer being inspected as well as any previously formed layers under the inspected layer may be substantially the same for the programmed defects as for device structures of the inspected layer. In this manner, in one embodiment, characteristics of one or more layers formed in the dummy area under a layer inspected in the wafer inspection process are substantially the same as the characteristics of the one or more layers formed in device areas of the production chip.

An inspection toot's optimum mode of inspection (where mode=some combination of parameter values such as wavelength, pixel size or magnification, aperture, focus value, polarization, light power, etc.) can then be chosen using the programmed defects. For example, the method also includes scanning the dummy area of a wafer on which the altered design is printed with two or more optical modes of an inspection system, as shown in step 502 of FIG. 5, thereby generating output with one or more detectors of the inspection for each of the two or more optical modes. In one embodiment, scanning the dummy area includes scanning only known locations of the defects in the dummy area. For example, the scanning may include driving to the known locations of various programmed defects and generating output at those locations. The scanning may be performed in any suitable manner, and the inspection system may be configured as described further herein.

If more than one mode of the inspection system used for this scanning step can be used to generate output for the wafer simultaneously, then at least some of the output generated in this step may be generated for different modes simultaneously. However, if more than one mode of the inspection system used for this scanning step cannot be used to generate output for the wafer simultaneously, then the scanning may include repeatedly scanning the dummy area until all of the modes that are being tested have generated output. For example, the scanning step may include scanning the dummy area with one or more modes, then altering one or more values of one or more parameters of the inspection system such that scanning can be performed with one or more other modes. Then, scanning can be performed with those other mode(s).

In one embodiment, the two or more optical modes used to scan the dummy area include all optical modes available on the inspection system. In an additional embodiment, the two or more optical modes used to scan the dummy area include only a portion of all optical modes available on the inspection system. For example, the output may be generated in the dummy area across all the programmed defect types with some or all of the modes that are available on the inspector. In one such example, if one or more of the modes available on the inspection system are known a priori to be unsuitable for all of the defect types of interest on a given wafer, those modes may not be used for any of the scanning steps described herein.

In some embodiments, the output generated during scanning of the dummy area includes defect signal data for the defects. For example, scanning the dummy area may include driving to the known locations of the various programmed defects and collecting defect signal data across all or some of the modes that are available on the inspector.

Figure 5:
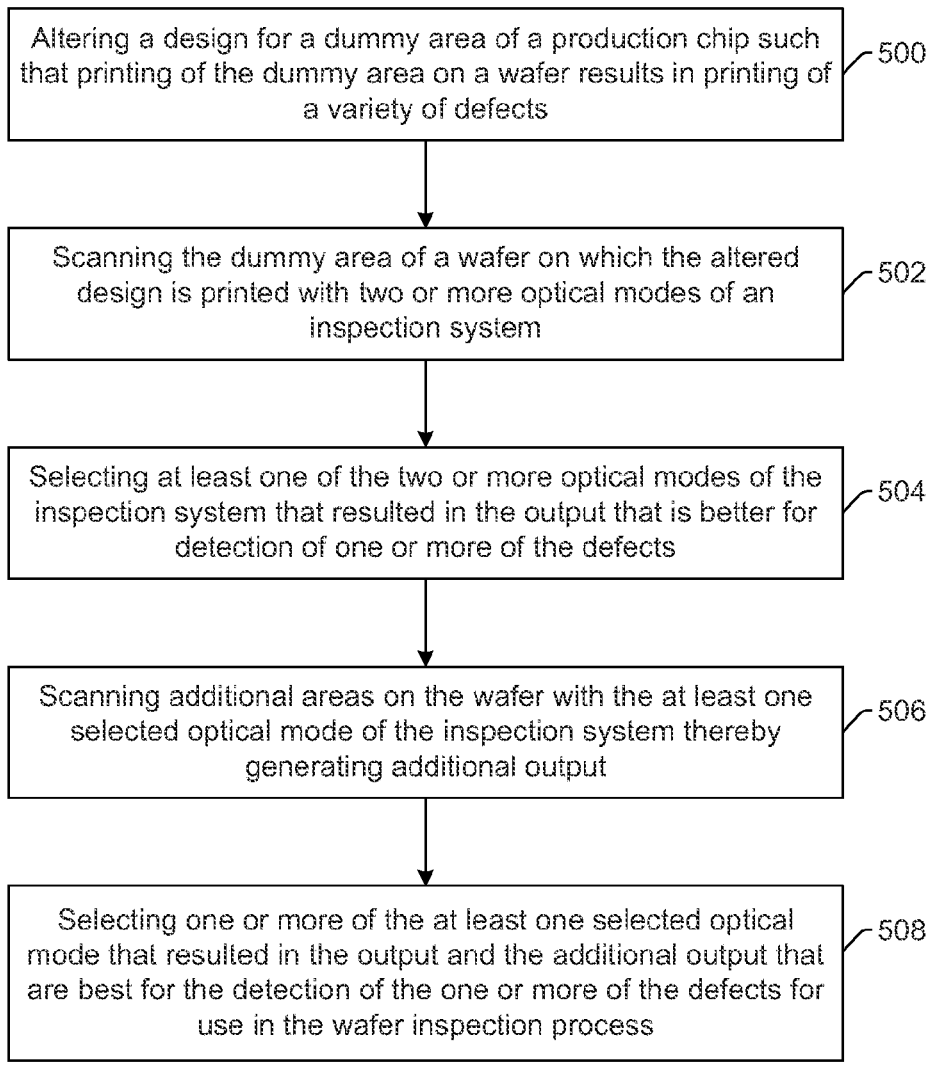
FIG. 5 is a flow chart illustrating one embodiment of a method for setting up a wafer inspection process.

As shown in step 504 of FIG. 5, the method also includes selecting at least one of the two or more optical modes of the inspection system that resulted in the output that is better for detection of one or more of the defects than the output produced by others of the two or more optical modes. In one embodiments, the output that is better for the detection of the one or more defects includes the defect signal data having the highest value or values. In another embodiment, scanning the dummy area and selecting at least one of the two or more optical modes are performed automatically. In one example, a computer subsystem (or system) configured as described herein may be configured to compare the defect signal data generated by each of the modes used for scanning a defect (on a defect-by-defect basis). In this manner, the mode or modes that generated the highest defect signal data for each defect may be determined by the comparing step. Each of the modes that generated the highest defect signal data for at least one of the programmed defects may be used in the next scanning step that will now be described.

As shown in step 506 of FIG. 5, the method further includes scanning additional areas on the wafer with the at least one selected optical mode of the inspection system thereby generating additional output with the inspection system. In one embodiment, the additional output generated during scanning the additional areas includes noise information for the wafer. In another embodiment, the additional areas on the wafer include at least an entirety of the production chip. In an additional embodiment, the additional areas on the wafer include an entirety of an area of the wafer that will be inspected in the wafer inspection process. For example, in some instances, an entirety of a production chip may not be scanned in an inspection process. In such instances, the additional area that is scanned may include at least (or just) the areas of the production chip that will be scanned in the inspection process once it is setup.

By scanning a significant area of the functional chip pattern (as opposed to just the dummy pattern) with the highest signal modes (as found using the dummy pattern programmed defects), the inspection system can be used to gather noise information. In this manner, the method may include scanning the rest of the chip or wafer for the worst case noise to allow selection or correction of the best mode(s) based on the signal versus worst case noise (as opposed to the signal versus local noise). In another embodiment, scanning the additional areas is performed automatically. In this manner, this step may also be automated.

The method also includes selecting one or more of the at least one selected optical mode that resulted in the output and the additional output that are best for the detection of the one or more of the defects for use in the wafer inspection process, as shown in step 508 of FIG. 5. For example, the best mode (or modes) can be chosen by determining which mode (or modes) has (or have) the highest signal to noise values after dividing signal/noise for each mode on each programmed defect type and/or location. This step may also be automated. Therefore, the embodiments described herein allow the mode selection step in recipe setup to go from manual or semi-manual (and slow) as performed today to automatic (and fast) using the embodiments described herein.

The selecting steps described above, and any other steps described herein, may be performed depending on the types of defects that are to be detected in the wafer inspection process. For example, the same mode(s) may not produce the best defect signal-to-noise for more than one defect type. In this case, selecting at least one of the two or more optical modes that is better for detection of one or more of the defects may result in the selection of one set of modes for one defect type, another set of modes for another defect type, and so on. In this manner, in some embodiments, selecting at least one of the two or more optical modes includes selecting a first of the two or more optical modes that is better for the detection of a first of the one or more defects and a second of the two or more optical modes that is better for detection of a second of the one or more defects. In addition, selecting one or more of the at least one selected optical mode that are best for the detection of the one or more of the defects may result in the selection of one mode for one defect type and another mode for another defect type. In one such embodiment, selecting one or more of the at least one selected optical mode includes selecting different optical modes, each of which is best for the detection of only some of the one or more defects, for use in the wafer inspection process.

For each production chip's inspection layer, a recipe sensitivity metric can be outputted to the user. In addition, for each mode on an inspector, the tool may use the programmed defects to output data showing which defect types can be caught with a high, medium, or low capture rate, which may be shown by different colors in output such as a chart or table. For example, for each optical mode being considered in the method, a table may be generated that includes a row of different defect types such that each different defect type has a column in the table. The table may also include rows for the various defect characteristics being considered under the defect type row. For example, the table may include different rows, one for each defect size being considered. The table may also include a row for various defect locations under the various defect characteristic rows such that different defect locations may be shown as sub-columns in this row. Therefore, the defect location row may include different sub-columns that correspond to the defect type of the column in which it is included placed on different background pattern locations such as those shown in FIG. 2.

The content of each cell in the table under the defect type row may be a color indicating the caprate (capture rate) for a particular combination of defect type, characteristic, and location. For example, a green color may be used to represent a caprate greater than 80%, a yellow color may be used to represent a caprate between 50% and 80%, and a red color may be used to represent a caprate that is less than 50%. This type of data can be used to decide which mode(s) need to be run in order to catch which defect types and sizes. For example, if a user feels their inspector must be able to detect a round or circular defect having a size greater than or equal to 13 nm in a particular background pattern with a caprate of greater than 80% (meaning 8 out of 10 such defects can be caught), then the mode that would be capable of such defect detection can be easily determined using a table or chart as described above.

The methods described herein may also include any other steps involved in wafer inspection process setup. For example, the methods may include determining or selecting alignment sites for the wafer inspection process, which may include determining or selecting alignment marks on the wafer. The alignment sites and/or marks are preferably selected such that the wafer inspection process determines defect locations with relatively accurate x, y coordinates. The wafer inspection setup may also include care area selection or determination. The care areas may be selected to include critical areas on the wafer while do not care areas may include non-critical areas on the wafer and dummy pattern areas on the wafer. Wafer inspection setup may also include a light box step in which the best light power for inspection is selected. In addition, wafer inspection setup may include threshold selection in which a threshold (e.g., a gray level pixel value) that separates defects from nuisance is determined. Wafer inspection setup may further include setting up a binning process for the wafer inspection process. Binning may be performed to separate defects from nuisances (e.g., using detector images of the detected events on the wafer). The inspector mode selection (and other recipe setup steps) can be automated.

The altering and selecting steps of the method described above are performed with one or more computer systems, which may be configured as described further herein.

The embodiments described herein have a number of advantages over currently used methods for setting up wafer inspection processes. For example, the embodiments described herein enable faster selection of the best modes for each pattern defect type thereby saving expensive tool time. The embodiments described herein also provide more reliable selection of the best mode(s) for each pattern detect type thereby reducing the risk of missing yield loss. For example, the embodiments described herein can aid setup and sensitivity of wafer inspection systems that are used in semiconductor fabrication plants worldwide. Fabs often compete with each other for business from fabless chip makers. If killer defect types are missed, it can mean the loss of hundreds of millions of dollars of business to a competitor fab. The embodiments described herein reduce the chances of that "miss" happening. Although the percentage of risk reduction is very difficult to quantify, even if only a 1% risk reduction occurs, this would be of one million dollars in value for every foundry fab in the world. In addition, the embodiments described herein provide quantifiable pattern defect sensitivity per defect size on each chip, layer, and defect type combination thereby reducing risk and cost. Furthermore, the embodiments described herein reduce the wafers and SEM review time needed for inspection system recipe setup thereby reducing the cost of wafer inspection recipe setup.

Each of the embodiments of the methods described above may include any other step(s) of any other method(s) described herein. Furthermore, each of the embodiments of the methods described above may be performed by any of the systems described herein.

All of the methods described herein may include storing results of one or more steps of the method embodiments in a non-transitory computer-readable storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. For example, after the method selects one or more modes that are best for use in the wafer inspection process, the method may include storing information about the selected mode(s) in a storage medium.

An additional embodiment relates to a non-transitory computer-readable medium storing program instructions executable on a computer system for performing a computer-implemented method for setting up a wafer inspection process. One such embodiment is shown in FIG. 3. In particular, as shown in FIG. 3, non-transitory computer-readable medium 300 includes program instructions 302 executable on computer system 304. The computer-implemented method includes the steps of the method described above. The computer-implemented method for which the program instructions are executable may include any other step(s) described herein.

Program instructions 302 implementing methods such as those described herein may be stored on computer-readable medium 300. The computer-readable medium may be a storage medium such as a magnetic or optical disk, a magnetic tape, or any other suitable non-transitory computer-readable medium known in the art.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), or other technologies or methodologies, as desired.

The computer system may take various forms, including a personal computer system, image computer, mainframe computer system, workstation, network appliance, Internet appliance, or other device. In general, the term "computer system" may be broadly defined to encompass any device having one or more processors, which executes instructions from a memory medium. The computer system may also include any suitable processor known in the art such as a parallel processor. In addition, the computer system may include a computer platform with high speed processing and software, either as a standalone or a networked tool.

Another embodiment relates to a wafer inspection system. One embodiment of such a tool is shown in FIG. 4. The wafer inspection system includes one or more computer subsystems configured for altering a design for a dummy area of a production chip such that printing of the dummy area on a wafer results in printing of a variety of defects. Two or more of the defects have different types, one or more different characteristics, different contexts in the design, or a combination thereof. The computer subsystem(s) may be configured to alter the design as described further herein.

In one embodiment, as shown in FIG. 4, the wafer inspection system includes computer subsystem 414. In the embodiment shown in FIG. 4, the computer subsystem is coupled to optical subsystem 400. For example, the computer subsystem may be coupled to a detector of the optical subsystem. In one such example, as shown in FIG. 4, computer subsystem 414 is coupled to detector 412 of optical subsystem 400 (e.g., by one or more transmission media shown by the dashed lines in FIG. 4, which may include any suitable transmission media known in the art). The computer subsystem may be coupled to the detector in any suitable manner. The computer subsystem may be coupled to the optical subsystem in any other suitable manner such that image(s) and any other information for the wafer generated by the optical subsystem can be sent to the computer subsystem and, optionally, such that the computer subsystem can send instructions to the optical subsystem to perform one or more steps described herein.

Alternatively, the computer subsystem(s) included in the system may include a computer subsystem coupled to an optical subsystem of the wafer inspection system and/or a computer subsystem that is not coupled to the optical subsystem. In this manner, one of the computer subsystems may be a stand alone type computer subsystem, which may be coupled to the computer subsystem of the wafer inspection system. For example, a stand alone type computer subsystem may be configured to alter the design as described herein and a computer subsystem coupled to an optical subsystem of a wafer inspection system may be configured to perform other steps described herein. In one such example, the stand alone type computer subsystem may be part of another tool such as an electronic design automation (EDA) tool.

The wafer inspection system also includes an optical subsystem configured to scan the dummy area of a wafer on which the altered design is printed with two or more optical modes of the optical subsystem thereby generating output with one or more detectors of the optical subsystem for each of the two or more optical modes. For example, as shown in FIG. 4, the wafer inspection tool includes optical subsystem 400.

As further shown in FIG. 4, the optical subsystem includes light source 404. Light source 404 may include any suitable light source known in the art such as a broadband plasma light source. Light source 404 is configured to direct light to beam splitter 406, which is configured to reflect the light from light source 404 to refractive optical element 408. Refractive optical element 408 is configured to focus light from beam splitter 406 to wafer 410. Beam splitter 406 may include any suitable beam splitter such as a 50/50 beam splitter. Refractive optical element 408 may include any suitable refractive optical element, and although refractive optical element 408 is shown in FIG. 4 as a single refractive optical element, it may be replaced with one or more refractive optical elements and/or one or more reflective optical elements.

Light source 404, beam splitter 406, and refractive optical element 408 may, therefore, form an illumination channel for the optical subsystem. The illumination channel may include any other suitable elements (not shown in FIG. 4) such as one or more polarizing components and one or more filters such as spectral filters. As shown in FIG. 4, the light source, beam splitter, and refractive optical element are configured such that the light is directed to the wafer at a normal or substantially normal angle of incidence. However, the light may be directed to the wafer at any other suitable angle of incidence.

The optical subsystem may be configured to scan the light over the wafer in any suitable manner.

Light reflected from wafer 410 due to illumination may be collected by refractive optical element 408 and directed through beam splitter 406 to detector 412. Therefore, the refractive optical element, beam splitter, and detector may form a detection channel of the optical subsystem. The detector may include any suitable imaging detector known in the art such as a charge coupled device (CCD). This detection channel may also include one or more additional components (not shown in FIG. 4) such as one or more polarizing components, one or more spatial filters, one or more spectral filters, and the like. Detector 412 is configured to generate output that is responsive to the reflected light detected by the detector. The output may include signals, signal data, images, image data, and any other suitable output.

As described above, the detector included in the optical subsystem may be configured to detect light reflected from the wafer. Therefore, the detection channel included in the optical subsystem may be configured as a bright field (BF) channel. However, the optical subsystem may include one or more detection channels (not shown) that may be used to detect light scattered from the wafer due to illumination of the wafer. In addition, one or more parameters of the detection channel shown in FIG. 4 may be altered such that the detection channel detects light scattered from the wafer. In this manner, the optical subsystem may be configured as a dark field (DF) tool and/or a BF tool.

The optical subsystem may be configured to have more than one mode in any suitable manner. In some instances, the optical subsystem can have more than one mode simultaneously (e.g., if the optical subsystem includes more than one illumination channel (not shown in FIG. 4) and/or more than one detection channel (not shown in FIG. 4)). In other instances, the optical subsystem can have more than one mode sequentially (e.g., by changing one or more parameters of an illumination channel such as illumination wavelength(s), polarization(s), angle(s), etc. and/or a detection channel such as detection wavelength(s), polarization(s), angle(s), etc. between scans of a wafer). Furthermore, the optical subsystem can have some modes simultaneously and other modes sequentially. The wafer inspection system may be configured to control the optical mode(s) used for any scan of any wafer in any suitable manner.

Computer subsystem 414 is configured for detecting defects on the wafer based on the output generated by the optical subsystem. The computer subsystem may be configured to detect the defects on the wafer in any suitable manner.

The computer subsystem(s) included in the wafer inspection system are also configured for selecting at least one of the two or more optical modes of the optical subsystem that resulted in the output that is better for detection of one or more of the defects than the output produced by others of the two or more optical modes, which may be performed as described herein. The optical subsystem is also configured to scan additional areas on the wafer with the at least one selected optical mode of the optical subsystem thereby generating additional output with the optical subsystem, which may be performed as described further herein. The computer subsystem(s) are further configured for selecting one or more of the at least one selected optical mode that resulted in the output and the additional output that are best for the detection of the one or more of the defects for use in the wafer inspection process, which may be performed as described further herein. In addition, the computer subsystem(s) and the optical subsystem may be configured to perform any other step(s) described herein. The wafer inspection system shown in FIG. 4 may be further configured as described herein.

It is noted that FIG. 4 is provided herein to generally illustrate one configuration of an optical subsystem that may be included in the wafer inspection system embodiments described herein. Obviously, the configuration of the optical subsystem described herein may be altered to optimize the performance of the system as is normally performed when designing a commercial inspection system. In addition, the wafer inspection systems described herein may be implemented using an existing optical subsystem (e.g., by adding functionality described herein to an existing inspection system) such as the 28XX, 29XX, and Puma 9XXX series of tools that are commercially available from KLA-Tencor, Milpitas. Calif. For some such systems, the methods described herein may be provided as optional functionality of the system (e.g., in addition to other functionality of the system). Alternatively, the wafer inspection systems described herein may be designed "from scratch" to provide a completely new system.

Further modifications and alternative embodiments of various aspects of the invention will be apparent to those skilled in the art in view of this description. For example, methods and systems for setting up a wafer inspection process using programmed defects are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for setting up a wafer inspection process, comprising:

altering a design for a dummy area of a production chip such that printing of the dummy area on a wafer results in printing of a variety of defects, wherein two or more of the defects have different types, one or more different characteristics, different contexts in the design, or a combination thereof;

scanning the dummy area of a wafer on which the altered design is printed with two or more optical modes of an inspection system thereby generating output with one or more detectors of the inspection system for each of the two or more optical modes;

selecting at least one of the two or more optical modes of the inspection system that resulted in the output that is better for detection of one or more of the defects than the output produced by others of the two or more optical modes;

scanning additional areas on the wafer with the at least one selected optical mode of the inspection system thereby generating additional output with the inspection system; and selecting one or more of the at least one selected optical mode that resulted in the output and the additional output that are best for the detection of the one or more of the defects for use in the wafer inspection process, wherein the altering and selecting steps are performed with one or more computer systems.

2. The method of claim 1, wherein the defects are pattern defects, and wherein altering the design comprises adding patterned features, removing patterned features or adding and removing patterned features in the design for the dummy area.

3. The method of claim 1, wherein the production chip is not a test chip.

4. The method of claim 1, wherein the dummy area is not a scribe line area on the wafer.

5. The method of claim 1, wherein the additional areas on the wafer comprise at least an entirety of the production chip.

6. The method of claim 1, wherein the additional areas on the wafer comprise an entirety of an area of the wafer that will be inspected in the wafer inspection process.

7. The method of claim 1, wherein characteristics of one or more layers formed in the dummy area under a layer inspected in the wafer inspection process are substantially the same as the characteristics of the one or more layers formed in device areas of the production chip.

8. The method of claim 1, wherein scanning the dummy area comprises scanning only known locations of the defects in the dummy area.

9. The method of claim 1, wherein the two or more optical modes used to scan the dummy area comprise all optical modes available on the inspection system.

10. The method of claim 1, wherein the two or more optical modes used to scan the dummy area comprise only a portion of all optical modes available on the inspection system.

11. The method of claim 1, wherein the output generated during scanning the dummy area comprises defect signal data for the defects.

12. The method of claim 11, wherein the output that is better for the detection of the one or more defects comprises the defect signal data having the highest value or values.

13. The method of claim 1, wherein scanning the dummy area and selecting at least one of the two or more optical modes are performed automatically.

14. The method of claim 1, wherein the additional output generated during scanning the additional areas comprises noise information for the wafer.

15. The method of claim 1, wherein scanning the additional areas is performed automatically.

16. The method of claim 1, wherein the different contexts in the design comprise different patterned features that have the same characteristics as corresponding patterned features in a device area of the production chip.

17. The method of claim 1, wherein selecting at least one of the two or more optical modes comprises selecting a first of the two or more optical modes that is better for the detection of a first of the one or more defects and a second of the two or more optical modes that is better for detection of a second of the one or more defects.

18. The method of claim 1, wherein selecting one or more of the at least one selected optical mode comprises selecting different optical modes, each of which is best for the detection of only some of the one or more defects, for use in the wafer inspection process.

19. A non-transitory computer-readable medium, storing program instructions executable on a computer system for performing a computer-implemented method for setting up a wafer inspection process, wherein the computer-implemented method comprises:

altering a design for a dummy area of a production chip such that printing of the dummy area on a wafer results in printing of a variety of defects, wherein two or more of the defects have different types, one or more different characteristics, different contexts in the design, or a combination thereof;

scanning the dummy area of a wafer on which the altered design is printed with two or more optical modes of an inspection system thereby generating output with one or more detectors of the inspection system for each of the two or more optical modes;

selecting at least one of the two or more optical modes of the inspection system that resulted in the output that is better for detection of one or more of the defects than the output produced by others of the two or more optical modes;

scanning additional areas on the wafer with the at least one selected optical mode of the inspection system thereby generating additional output with the inspection system; and selecting one or more of the at least one selected optical mode that resulted in the output and the additional output that are best for the detection of the one or more of the defects for use in the wafer inspection process.

20. A wafer inspection system, comprising:

one or more computer subsystems configured for altering a design for a dummy area of a production chip such that printing of the dummy area on a wafer results in printing of a variety of defects, wherein two or more of the defects have different types, one or more different characteristics, different contexts in the design, or a combination thereof, wherein each of the one or more computer subsystems is a device having one or more processors, and wherein the device executes instructions from a memory medium; and an optical subsystem comprising an illumination channel configured to focus light to a wafer and one or more detectors configured to generate output responsive to light from the wafer detected by the one or more detectors, wherein the optical subsystem is configured to scan the light from the illumination channel over the dummy area of the wafer on which the altered design is printed with two or more optical modes of the optical subsystem thereby generating output with the one or more detectors of the optical subsystem for each of the two or more optical modes;

wherein the one or more computer subsystems are further configured for selecting at least one of the two or more optical modes of the optical subsystem that resulted in the output that is better for detection of one or more of the defects than the output produced by others of the two or more optical modes;

wherein the optical subsystem is further configured to scan additional areas on the wafer with the at least one selected optical mode of the optical subsystem thereby generating additional output with the optical subsystem; and wherein the one or more computer subsystems are further configured for selecting one or more of the at least one selected optical mode that resulted in the output and the additional output that are best for the detection of the one or more of the defects for use in the wafer inspection process.

21. The system of claim 20, wherein the defects are pattern defects, and wherein altering the design comprises adding patterned features, removing patterned features or adding and removing patterned features in the design for the dummy area.

22. The system of claim 20, wherein the production chip is not a test chip.

23. The system of claim 20, wherein the dummy area is not a scribe line area on the wafer.

24. The system of claim 20, wherein the additional areas on the wafer comprise at least an entirety of the production chip.

25. The system of claim 20, wherein the additional areas on the wafer comprise an entirety of an area of the wafer that will be inspected in the wafer inspection process.

26. The system of claim 20, wherein characteristics of one or more layers formed in the dummy area under a layer inspected in the wafer inspection process are substantially the same as the characteristics of the one or more layers formed in device areas of the production chip.

27. The system of claim 20, wherein the optical subsystem is further configured to scan the dummy area by scanning only known locations of the defects in the dummy area.

28. The system of claim 20, wherein the two or more optical modes used to scan the dummy area comprise all optical modes available on the optical subsystem.

29. The system of claim 20, wherein the two or more optical modes used to scan the dummy area comprise only a portion of all optical modes available on the optical subsystem.

30. The system of claim 20, wherein the output generated during scanning of the dummy area by the optical subsystem comprises defect signal data for the defects.

31. The system of claim 30, wherein the output that is better for the detection of the one or more defects comprises the defect signal data having the highest value or values.

32. The system of claim 20, wherein the optical subsystem is further configured to scan the dummy array automatically, and wherein selecting at least one of the two or more optical modes is performed automatically.

33. The system of claim 20, wherein the additional output comprises noise information for the wafer.

34. The system of claim 20, wherein the optical subsystem is further configured to scan the additional areas automatically.

35. The system of claim 20, wherein the different contexts in the design comprise different patterned features that have the same characteristics as corresponding patterned features in a device area of the production chip.

36. The system of claim 20, wherein selecting at least one of the two or more optical modes comprises selecting a first of the two or more optical modes that is better for the detection of a first of the one or more defects and a second of the two or more optical modes that is better for detection of a second of the one or more defects.

37. The system of claim 20, wherein selecting one or more of the at least one selected optical mode comprises selecting different optical modes, each of which is best for the detection of only some of the one or more defects, for use in the wafer inspection process.

* * * * *